(12) United States Patent
Wilson et al.

(10) Patent No.: US 6,921,396 B1
(45) Date of Patent: Jul. 26, 2005

(54) MULTI-LUMEN CATHETER WITH INTEGRATED CONNECTOR

(75) Inventors: Jon S. Wilson, Winston-Salem, NC (US); Kenneth T. Cassidy, Mocksville, NC (US); Mark C. Martel, Blues Creek, NC (US)

(73) Assignee: Arrow International, Inc., Reading, PA (US)

( * ) Notice: Subject to any disclaimer, the term of this patent is extended or adjusted under 35 U.S.C. 154(b) by 221 days.

(21) Appl. No.: 10/231,577

(22) Filed: Aug. 30, 2002

(51) Int. Cl.[7] ............................................. A61M 31/00
(52) U.S. Cl. ....................................... 604/508; 604/533
(58) Field of Search .............................. 604/19, 27, 29, 604/40, 500, 506–508, 510, 93.01, 94.01, 160, 161, 164.01, 164.04, 164.07, 164.09, 264, 523, 538, 533–535, 539, 284, 540, 950; 128/898

(56) References Cited

U.S. PATENT DOCUMENTS

| | | | |
|---|---|---|---|
| 4,134,402 A | 1/1979 | Mahurkar | |
| 4,299,228 A | 11/1981 | Peters | |
| 4,327,722 A | 5/1982 | Groshong et al. | |
| 4,432,752 A | 2/1984 | Marlon | |
| 4,453,928 A | 6/1984 | Steiger | |
| RE31,873 E | 4/1985 | Howes | |
| 4,543,087 A | 9/1985 | Sommercorn et al. | |
| 4,568,329 A | 2/1986 | Mahurkar | |
| 4,623,327 A | 11/1986 | Mahurkar | |
| 4,643,711 A | 2/1987 | Bates | |
| 4,675,004 A | 6/1987 | Hadford et al. | |
| 4,681,122 A | 7/1987 | Winters et al. | |
| 4,682,978 A | 7/1987 | Martin | |
| 4,692,141 A | 9/1987 | Mahurkar | |
| 4,772,268 A | 9/1988 | Bates | |

(Continued)

OTHER PUBLICATIONS

Instructions for Use (Copyright Dated 1990) for Polycath Polyurethane Central Venous Catheter; believed to have been packaged with product believed to have been sold in the United States before Jan. 2000 and related marketing materials.

Instructions for Use (Copyright Dated 1992) for FloLock Single Lumen Bi-directional Valved Catheter ; believed to have been packaged with product believed to have been sold in the United States before Jan. 2000.

(Continued)

*Primary Examiner*—Nicholas D. Lucchesi
*Assistant Examiner*—Michael M Thompson
(74) *Attorney, Agent, or Firm*—Amster Rothstein & Ebenstein, LLP

(57) ABSTRACT

A multi-lumen catheter and method for inserting same into a patient is disclosed. The catheter includes a multi-lumen catheter tube having a distal end, a proximal end, and a plurality of lumens therethrough. The catheter may include a single-lumen flush tube portion, the flush tube portion having a proximal end and a distal end, the proximal end of the flush tube portion being connected to the distal end of the catheter tube such that the single lumen of the flush tube portion is in fluid communication with each of the lumens in the catheter tube. A connector is provided having a proximal end, a distal end, and a longitudinal cavity extending therethrough. The cavity includes a coupling portion near the distal end of the connector, and the proximal end of the connector is connected to the distal end of the flush tube portion or the distal end of the catheter tube such that the cavity of the connector is in fluid communication with the single lumen of the flush tube portion or the plurality of lumens in the catheter tube. The coupling portion of the cavity of the connector is configured to receive a mating coupling portion of a medical device such as a trocar. The catheter device facilitates the subcutaneous tunneling of the catheter after catheter tip placement, and simultaneous fluid communication with all of the multiple catheter lumens.

34 Claims, 12 Drawing Sheets

U.S. PATENT DOCUMENTS

| | | |
|---|---|---|
| 4,772,269 A | 9/1988 | Twardowski et al. |
| 4,808,155 A | 2/1989 | Mahurkar |
| 4,832,687 A | 5/1989 | Smith, III |
| 4,895,561 A | 1/1990 | Mahurkar |
| 5,053,003 A | 10/1991 | Dadson et al. |
| 5,053,004 A | 10/1991 | Markel et al. |
| 5,053,023 A | 10/1991 | Martin |
| 5,059,170 A | 10/1991 | Cameron |
| 5,106,368 A | 4/1992 | Uldall et al. |
| 5,129,891 A | 7/1992 | Young |
| 5,171,227 A | 12/1992 | Twardowski |
| 5,190,520 A | 3/1993 | Fenton, Jr. et al. |
| 5,312,337 A | 5/1994 | Flaherty et al. |
| 5,342,386 A | 8/1994 | Trotta |
| 5,360,397 A | 11/1994 | Pinchuk |
| 5,380,276 A | 1/1995 | Miller et al. |
| 5,399,168 A | 3/1995 | Wadsworth, Jr. et al. |
| 5,417,668 A | 5/1995 | Setzer et al. |
| 5,423,768 A | 6/1995 | Folden |
| 5,431,661 A | 7/1995 | Koch |
| 5,472,432 A | 12/1995 | Martin |
| 5,509,897 A | 4/1996 | Twardowski et al. |
| 5,558,635 A | 9/1996 | Cannon |
| 5,599,328 A | 2/1997 | Stevens |
| 5,624,413 A | 4/1997 | Markel et al. |
| 5,632,729 A | 5/1997 | Cai et al. |
| 5,637,102 A | 6/1997 | Tolkoff et al. |
| 5,685,867 A | 11/1997 | Twardowski et al. |
| 5,704,915 A | 1/1998 | Melsky et al. |
| 5,718,678 A | 2/1998 | Fleming, III |
| 5,743,873 A | 4/1998 | Cai et al. |
| 5,772,643 A | 6/1998 | Howell et al. |
| 5,776,111 A | 7/1998 | Tesio |
| 5,797,869 A | 8/1998 | Martin et al. |
| 5,807,311 A | 9/1998 | Palestrant |
| 5,944,732 A | 8/1999 | Raulerson et al. |
| 5,947,953 A | 9/1999 | Ash et al. |
| 5,989,206 A | 11/1999 | Prosl et al. |
| 5,989,213 A | 11/1999 | Maginot |
| 6,033,382 A | 3/2000 | Basta |
| 6,074,374 A | 6/2000 | Fulton |
| 6,086,555 A | 7/2000 | Eliasen et al. |
| 6,113,572 A | 9/2000 | Gailey et al. |
| 6,156,016 A | 12/2000 | Maginot |
| 6,190,349 B1 | 2/2001 | Ash et al. |
| 6,190,371 B1 | 2/2001 | Maginot et al. |
| 6,206,849 B1 | 3/2001 | Martin et al. |
| 6,293,927 B1 | 9/2001 | McGuckin, Jr. |
| 6,342,120 B1 | 1/2002 | Basta |
| 6,428,513 B1 | 8/2002 | Abrahamson |
| 6,585,705 B1 | 7/2003 | Maginot et al. |
| 6,638,242 B2 | 10/2003 | Wilson et al. |
| 6,682,519 B1 * | 1/2004 | Schon .................. 604/508 |
| 2001/0041857 A1 | 11/2001 | Sansoucy |
| 2003/0088213 A1 * | 5/2003 | Schweikert et al. ........ 604/177 |
| 2003/0153898 A1 | 8/2003 | Schon et al. |

OTHER PUBLICATIONS

Instructions for Use (not dated) for Infuse–a–Cath Polyurethane Central Venous Catheter; believed to have been packaged with product believed to have been sold in the United States before Jan. 2000.

Pictures of device believed to be partial sample of a product believed to have been sold in the United States before Jan. 2000 with the Polycath and/or Infuse–a–Cath Instructions for Use.

Copending U.S. Appl. No. 10/251,411; entitled Multi–Lumen Catheter with Attacheble Hub, filed Sep. 20, 2002.

Copending U.S. Appl. No. 10/231,748; entitled Double–Y Shaped Multi–Lumen Catheter with Selectively Attachable Hubs, filed Aug. 30, 2002.

Copending U.S. Appl. No. 10/251,384; Apparatus and Method for Reverse Tunneling a Multi–Lumen Catheter in a Patient, filed Sep. 20, 2002.

Copending U.S. Appl. No. 10/612,532; entitled Multi–Lumen Catheter with Attachable Hub, filed Jul. 1, 2003.

Abandoned U.S. Appl. No. 10/086,033; entitled Multi–Lumen Catheter with Attacheble Hub, filed Jan. 24, 2001.

Instructions For Use For Diatek Cannon Catheter Product First Sold In United States Sep. 2001.

Believed to be an unpublished sketch of a conception by Dr. John Frusha; date of sketch believed to be Jun. 24, 1997.

* cited by examiner

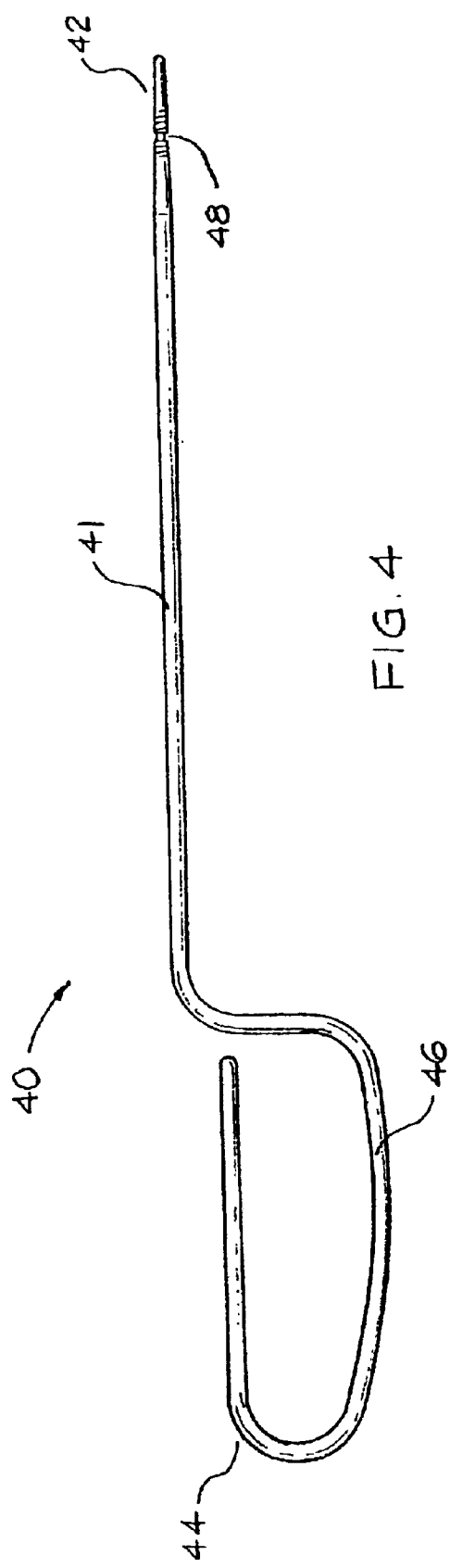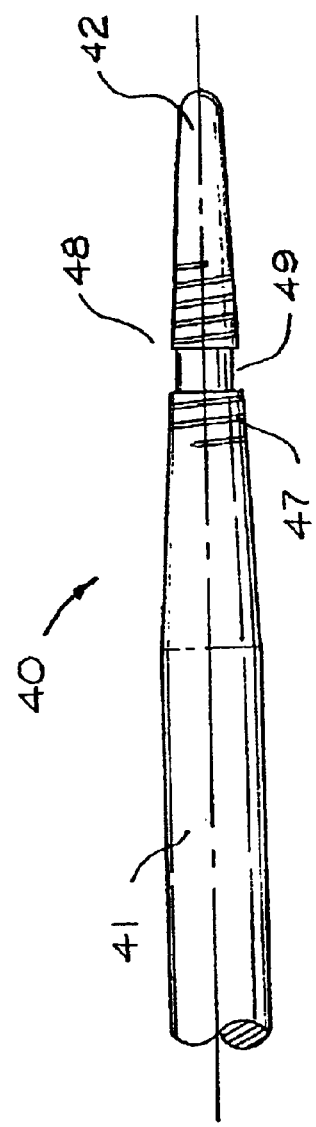
FIG. 4
FIG. 5

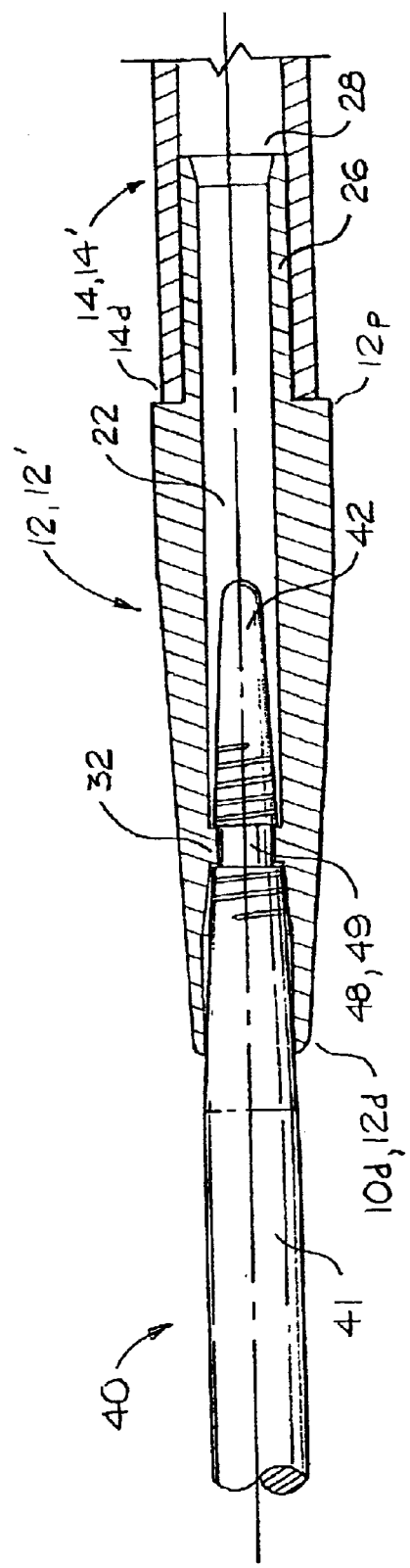
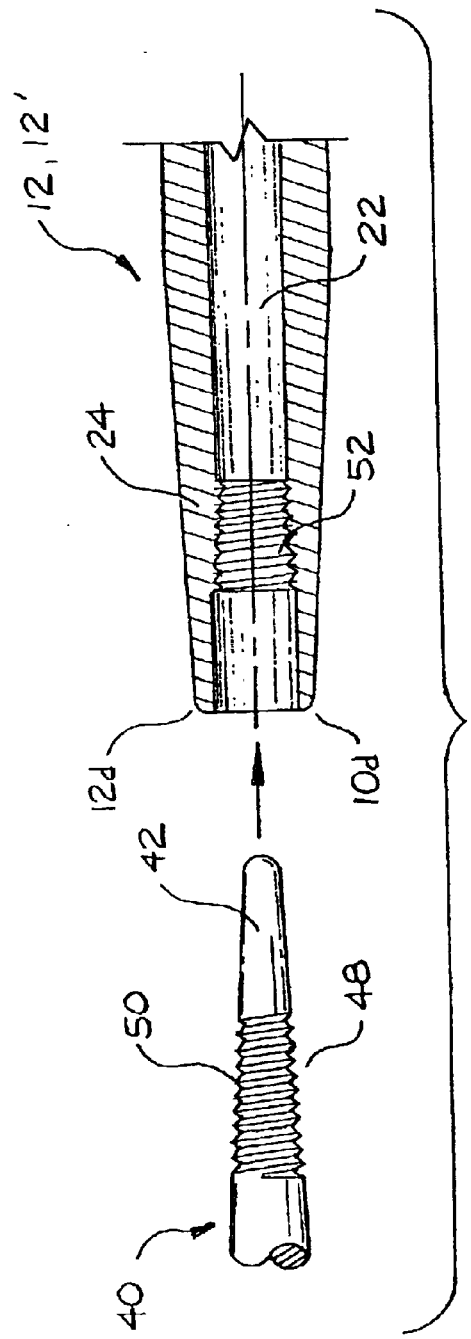

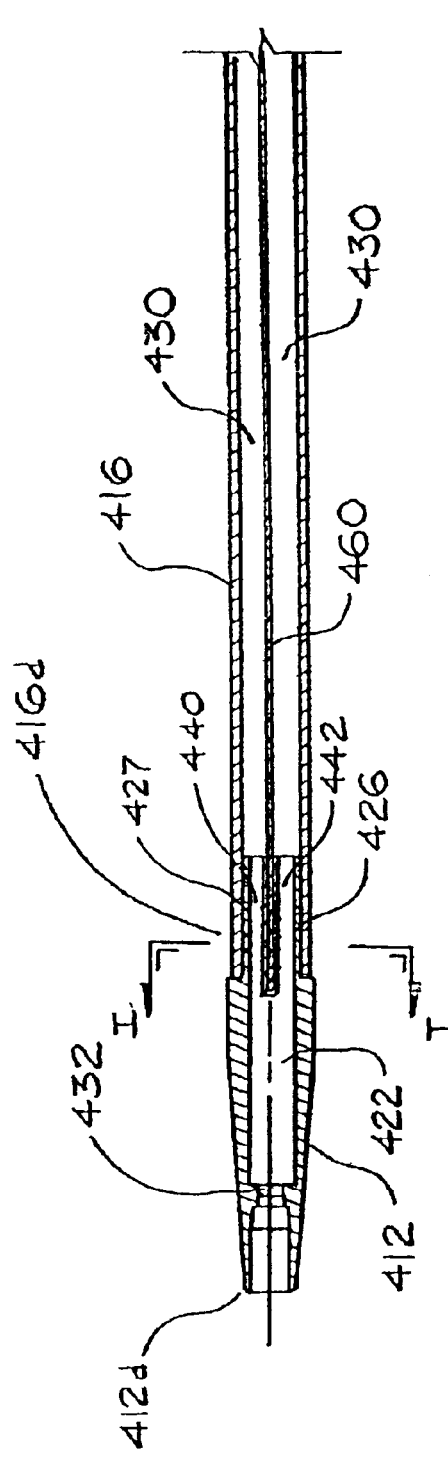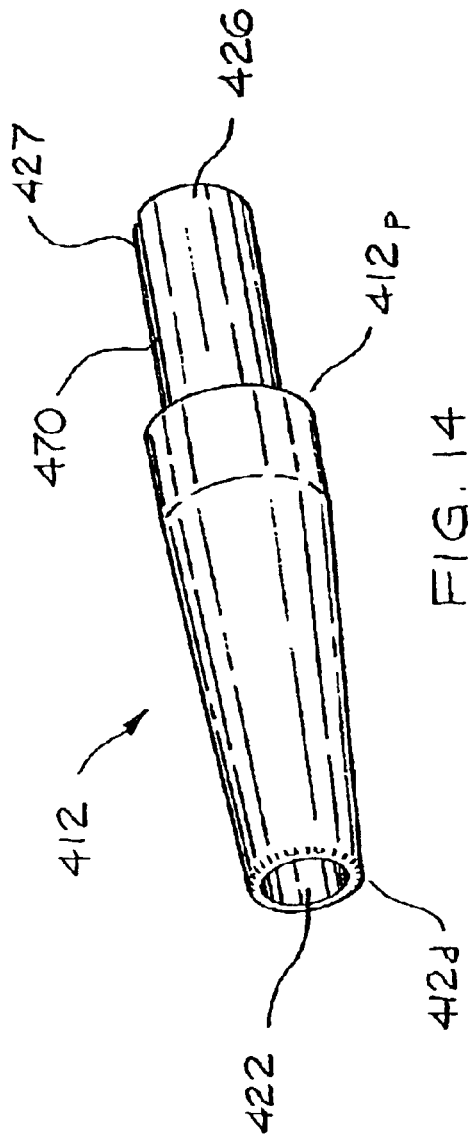

MULTI-LUMEN CATHETER WITH INTEGRATED CONNECTOR

BACKGROUND OF THE INVENTION

1) Field of the Invention

The present invention relates generally to medical instrumentation and more specifically to a multi-lumen catheter with an integrated connector that facilitates the subcutaneous tunneling of the catheter after catheter tip placement, and simultaneous fluid communication with all of the multiple catheter lumens.

2) Description of the Prior Art

Catheters, generally, are hollow, flexible tubes for insertion into a body cavity, duct, or vessel to allow the passage of fluids or distend a passageway. Catheters are often used for temporary or long-term dialysis treatment. Dialysis treatment provides for blood to be withdrawn from the patient, purified, and then returned to the patient. Thus, in dialysis treatment, catheters are used to allow passage of a patient's blood into and out of the patient's body. For optimal performance during dialysis treatment, the catheter tips, both in-flow and out-flow, should be placed in close proximity to the heart. Typically, medical personnel use either a double lumen catheter or two single lumen catheters. Both types, however, present certain deficiencies.

While double lumen catheters (e.g., U.S. Pat. No. 4,895,561) allow for a single venous insertion of the catheter into the desired vein, double lumen catheters typically do not permit optimal catheter tip placement. Due to differences among patients, optimal tip position varies from patient to patient. Non-optimal tip position may significantly lower flow values, resulting in less effective dialysis treatment. For current double lumen catheters, a physician must make an estimate regarding the appropriate catheter tube length prior to beginning the procedure of catheterization. Then, a subcutaneous tunnel is made from the preferred end position of the hub assembly, namely, away from the neck of the patient in order to allow for more convenient access to the dialysis treatment equipment. The double lumen catheter tube is then tunneled forwardly and the tips of the catheter are inserted into the area to be catheterized. The estimated catheter tube length and subsequent forward tunneling may result in less than optimal tip placement.

With the use of two independent catheters (e.g., U.S. Pat. No. 5,776,111 to Tesio) the problem of tip placement is addressed. The hub assembly of each catheter is removable from the tube and tip portion of the catheter, thereby allowing the catheter tip to be placed directly into the vein and advanced into the desired position. Then, the proximal end of the catheter can be reversed tunneled and trimmed to a desired length. Thereafter, the hub assembly is attached. Deficiencies, however, exist in this method of catheterization as well. One problem associated with this method is that this method requires two separate venous insertions, namely, two tunnels and two of each accessory instrument used for the procedure. Therefore, there is increased surgical time required to place two catheters, there are two wound entry sites which doubles the risk of post-surgical infection, and the two catheters together are significantly larger in diameter than one double lumen catheter.

Applicant's co-pending applications Ser. No. 09/769,052, filed Jan. 24, 2001, and Ser. No. 10/086,033, filed Feb. 28, 2002, disclose a multi-lumen catheter apparatus and method for inserting the apparatus in a patient. The disclosures of these co-pending applications are hereby incorporated by reference. In the disclosed apparatus and method, a multi-lumen catheter includes a selectively attachable hub assembly that allows the catheter tip to be positioned accurately within a patient's vein prior to subcutaneous tunneling. The distal end of the catheter tube is selectively attachable to the hub assembly. Accordingly, after the tips of the catheter have been accurately positioned in a patient, the other end of the catheter may be reverse tunneled under the skin of a patient. Specifically, after tip placement, an incision is made in the skin adjacent to the point where the protruding distal end of the catheter exits the skin. A subcutaneous tunnel is then formed having a first end at the incision and a second end exiting the skin at a point remote from the first end of the tunnel. The distal end of the catheter tube is passed through the subcutaneous tunnel and a tissue stabilizing cuff is seated therein, thereby stabilizing the tunneled portion of the catheter tube in the patient. A selectively attachable hub assembly is connected to the lumens at the distal tip of the catheter tube for subsequent connection of the catheter to a dialysis machine.

During the above procedure, guiding the distal end of the catheter tube through the subcutaneous tunnel can be problematic. It is known to engage the end of the catheter tube to a trocar extending through a subcutaneous tunnel for guiding the catheter tube through the tunnel with the trocar. Typically, however, a tip of the trocar includes barbs, ridges, threads, or the like for insertion into one of the lumens at the distal end of the catheter tube, thereby forming a friction or interference fit between the interior surface of the catheter and the barbs or ridges on the tip of the trocar. Unfortunately, the frictional engagement between the trocar tip and the catheter tube may be insufficient to withstand forces exerted on the catheter tube as the tube and adjoined trocar are passed through the tunnel, thereby causing the catheter tube to loosen and separate from the trocar. Also, because such a trocar engages only one lumen of a multi-lumen catheter, the shaft of the trocar and the catheter tube are not concentrically aligned, thereby forming a discontinuity which can impede passage of the trocar and adjoined catheter tube through the tunnel, and thereby increasing the likelihood of separation between the trocar and catheter tube.

The inventors are aware of a tunneling device that includes a trocar with a threaded tip for engagement in a connector that is releasably attached to the distal end of a multi-lumen catheter tube. One problems with this device included is that the connector is difficult to manipulate because of its small size. Also, use of this tunneling device necessarily required multiple steps, including: a) connecting one end of the connector to the end of the catheter tube; and b) connecting the other end of the connector to the tip of the trocar so that the catheter can be routed through a subcutaneous tunnel with the trocar. Though this tunneling device has proven to be adequately secure in most instances, the nature of the releasable attachment does not completely eliminate the possibility that the connector may disengage from the catheter tube as the connector and tube are guided through a subcutaneous tunnel via the trocar.

Therefore, there is a need for an improved connection between the trocar and the distal end of a multi-lumen catheter tube which provides more positive and aligned engagement between a trocar and the distal end of a multi-lumen catheter tube for guiding the catheter tube through a subcutaneous tunnel with a minimal number of separate component parts and process steps.

Another shortcoming of known apparatus and methods for catheterization of patients with multi-lumen catheters is the need to individually flush each of the multiple lumens of the catheter with a flushing solution to clear the lumens of debris, tissue, or the like prior to connection of the catheter to a dialysis machine. Flushing the lumens in a sequential manner adds time to the catheter insertion procedure. Known multi-lumen catheter systems described above also require sequential flushing of each of the multiple catheter lumens. Therefore, there is a need for an apparatus and method which permit simultaneous flushing of multiple catheter lumens in a multi-lumen catheter system.

SUMMARY OF THE INVENTION

A multi-lumen catheter includes a multi-lumen catheter tube having a distal end, a proximal end, and a plurality of lumens therethrough. The catheter may also include a single-lumen flush tube portion having a proximal end and a distal end. The proximal end of the flush tube portion is connected to the distal end of the catheter tube such that the single lumen of the flush tube portion is in fluid communication with each of the lumens in the catheter tube. The catheter further includes a connector having a proximal end, a distal end, and a longitudinal cavity extending therethrough. The cavity includes a coupling portion near the distal end of the connector, and the proximal end of the connector is connected to the distal end of the flush tube portion such that the cavity of the connector is in fluid communication with the single lumen of the flush tube portion. The coupling portion of the cavity of the connector is configured to receive a mating coupling portion of a trocar. The multi-lumen catheter tube, flush tube portion, and at least a portion of the connector near its proximal end may have substantially equal outer diameters. The multi-lumen catheter tube may include two lumens. A plurality of single-lumen extension tubes may be connected to the proximal end of the multi-lumen catheter tube such that each extension tube is in fluid communication with one of the plurality of lumens in the catheter tube. Each extension tube may include a tube wall having at least one opening configured to permit fluid flow into and from the catheter. At least one of the extension tubes may be shorter in length than at least one other extension tube.

The connector may be constructed of a material such as plastic, metal, or the like. The coupling portion of the connector cavity may include a collar portion configured to securely engage a groove in a coupling portion of a mating medical device. Alternatively, the coupling portion of the connector cavity may include a plurality of female threads configured to securely engage a plurality of male threads on a coupling portion of a mating medical device. The coupling portion of the connector may be configured for secure connection to a trocar, a syringe or other flushing device, or the like. The multi-lumen catheter may also include a stabilizing cuff on an outer portion of the catheter tube.

The connector also may include a body having proximal end and a distal end, and a spigot extending longitudinally from the proximal end of the body. The spigot may be sized and shaped for fitting engagement in the single lumen at the distal end of the flush tube portion, and the spigot may be affixed in the single lumen of the flush tube portion by a suitable adhesive. The connector may have a substantially tapered outer shape wherein the connector has a first outer diameter near its proximal end which is larger than a second outer diameter near its distal end. The first outer diameter of the connector may be substantially equal to an outer diameter of the flush tube portion, and the proximal end of the flush tube portion may be fused to the distal end of the catheter tube such as by heat welding or the like. A tissue in-growth stabilizing cuff may be affixed to an outer portion of the catheter tube. Preferably, the cuff may be positioned nearer to the distal end of the catheter than to the proximal end of the catheter.

In another arrangement, a multi-lumen catheter includes a multi-lumen catheter tube having a distal end, a proximal end, and a plurality of lumens therethrough, and a connector having a proximal end, a distal end, a plurality of prongs longitudinally extending from the proximal end of the connector. The plurality of prongs correspond in number to the plurality of lumens in the catheter tube. A longitudinal cavity is provided in the distal end of the connector and includes a coupling portion in the cavity. Each of the prongs is engaged in one of the lumens at the distal end of the catheter tube, thereby connecting the proximal end of the connector to the distal end of the catheter tube. The coupling portion of the longitudinal cavity of the connector is configured to receive a mating coupling portion of a medical device. The multi-lumen catheter tube may include two lumens therethrough and the connector may include two corresponding prongs. Where two lumens and two prongs are included, the lumens and prongs may have corresponding D-shaped cross sections for mating engagement therebetween. Each of the prongs may include a longitudinal passage therethrough, such that each of the passages is in fluid communication with the longitudinal cavity in the distal end of the connector. The passages and cavity combine to provide a plurality of substantially parallel flow paths through the connector from the distal end of the connector to the plurality of lumens in the catheter tube. Each of the prongs may be adhesively attached to inner walls of a corresponding lumen at the distal end of the catheter tube. Alternatively, each of the prongs may include a non-smooth outer contour, thereby providing a frictional fit between each of the prongs and inner walls of a corresponding lumen at the distal end of the catheter tube.

A trocar is provided which is configured for forming a subcutaneous tunnel and for secure engagement with the connector. The trocar may include a shaft having a handle end and an insertion end. The insertion end of the trocar may include a substantially tapered portion and an insertion tip. The trocar may further include a circumferential groove in the substantially tapered portion of the shaft near the insertion tip, wherein the circumferential groove is configured for secure engagement with an integrated connector on a distal end of a catheter. The trocar may also include a plurality of spiral grooves or threads in the substantially tapered portion of the shaft proximate the circumferential groove, the grooves or threads being configured to advance the insertion tip of the trocar into a bore in the integrated connector as the trocar is rotated relative to the connector. The handle end of the trocar may include a handle configured to be gripped by a person's hand.

A method is also provided for inserting and securing a multi-lumen catheter as described above in a patient. The method includes making an incision and inserting a proximal portion of the catheter into a body cavity or blood vessel such that distal portions of the multi-lumen catheter tube, the flush tube portion, and the connector extend outwardly from the patient through the first incision. A subcutaneous tunnel is formed having a first end proximate to the incision, and an opposed second end which is remote from the first end. A trocar is inserted through the tunnel such that at least a portion of the trocar protrudes from the first end of the tunnel. The trocar includes a coupling portion near a protruding tip of the trocar, and the coupling portion of the trocar is engaged in the coupling portion of the connector. The connector, the flush tube portion, and at least a portion of the distal end of the catheter tube are guided through the tunnel and out through the second end of the tunnel with the trocar until the catheter tube is finally positioned within the tunnel. The connector and engaged trocar, the flush tube portion, and a portion of the catheter tube near its distal end are severed from a remaining portion of the catheter tube once the catheter is in a final position.

Optionally, the catheter tube installed by the above method may include an in-growth stabilizing cuff affixed to a portion of an outer surface of the protruding distal portion of the catheter tube. When a stabilizing cuff is included on the catheter tube, the method may further include dilating a portion of the tunnel between the first end of the tunnel and a cuff seating point in the tunnel. A portion of the tunnel may be dilated by sliding a sheath dilator having a hollow bore over the insertion tip of the trocar and guiding the sheath dilator along the shaft of the trocar and into the first end of the tunnel. In this arrangement, the sheath dilator includes an outer dilating surface which has a larger diameter than a diameter of the trocar shaft. The sheath dilator is passed along the trocar and into the tunnel until the tunnel is sufficiently dilated between its first end and the cuff seating point. A catheter tube with a stabilizing cuff is seated in the tunnel when the stabilizing cuff is positioned at the cuff seating point in the tunnel. In another embodiment, the method may further include flushing the catheter lumens by injecting a flushing liquid through the distal end of the connector, the connector cavity, and the flush tube portion before engaging the coupling portion of the trocar in the coupling portion of the connector.

In order to provide distal portions of the catheter with a smooth outer profile to facilitate uninterrupted passage of the catheter through the subcutaneous tunnel, a tapered sheath may be placed around the connector and at least a portion of the adjoined flush tube portion. Preferably, the sheath includes a hollow bore for sliding engagement over the connector and flush tube portion, a tapered portion proximate to a distal end of the sheath, and a smooth outer surface. The smoothly-contoured sheath covers at least portion of the trocar shaft, the connector, and at least a portion of the flush tube portion, thereby covering and smoothing the discrete transitions between the adjoined components of the tunneling assembly. Placement of the sheath may include back-fitting the sheath over the trocar before engaging the coupling portion of the trocar in the coupling portion of the connector, and sliding the sheath over at least a portion of the trocar, the connector, and at least a portion of the flush tube portion.

For connecting the multi-lumen catheter to a fluid management device, the method may include providing a selectively attachable hub assembly including a hub body with a distal portion and a proximal portion. The proximal portion of the hub body is selectively attached to a distal portion of the remaining portion of the multi-lumen catheter tube. The proximal portion of the hub assembly is attached to a fluid management device.

A compression cover and compression sleeve can be preloaded onto the trocar by placing the compression cover and the compression sleeve axially over the tip of the trocar. A protrusion, such as a small piece of tape, can be wrapped around the trocar between the tip 42 and the preloaded compression cover and compression sleeve from inadvertently sliding off the trocar before the trocar and the connector are connected. Before the connector, flush tube portion, and distal portion of the catheter tube are severed from the remainder of the catheter tube, the compression cover and the compression sleeve are moved from the trocar onto the distal portion of the catheter tube.

The invention also provides a method for replacing a multi-lumen catheter tunneled as described above in a patient. The replacement method includes withdrawing distal portions of the catheter tube from the subcutaneous tunnel through the first end of the tunnel, and withdrawing the proximal end of the multi-lumen catheter tube from the patient. A replacement multi-lumen catheter is provided which includes a multi-lumen catheter tube having a proximal end with proximal tips and a distal end, a single-lumen flush tube portion having a proximal end connected to the distal end of the catheter tube and a distal end, and an integrated connector including a coupling portion on a distal end of the connector and having a proximal end connected to the distal end of the flush tube portion. The proximal end of the catheter tube of the replacement multi-lumen catheter is inserted through a replacement incision in the patient's skin proximate to the first end of the tunnel, and the proximal tips of the replacement multi-lumen catheter are placed in the patient such that a distal portion of the multi-lumen catheter tube, the flush tube portion, and the connector of the replacement multi-lumen catheter extend outwardly from the patient through the replacement incision. A trocar is extended through the subcutaneous tunnel such that at least a portion of the trocar protrudes from the patient through the first end of the tunnel, wherein the trocar includes a coupling portion near a protruding tip of the trocar. The coupling portion of the trocar is engaged in the coupling portion of the connector of the replacement multi-lumen catheter. The connector, the flush tube portion, and at least a portion of the distal end of the catheter tube of the replacement multi-lumen catheter are guided through the tunnel and out through the second end of the tunnel with the trocar until the replacement catheter tube is finally positioned in the tunnel. The connector and engaged trocar, the flush tube portion, and a distal portion of the multi-lumen catheter tube of the replacement multi-lumen catheter are severed from a remaining portion of the multi-lumen catheter tube of the replacement catheter. The replacement catheter is then connected to a fluid management device.

These and other aspects of the invention will be made clear from a reading the following detailed description together with the drawings.

BRIEF DESCRIPTION OF THE DRAWINGS

FIG. 4 is an elevation view of a trocar for use with the catheter of FIG. 1;

FIG. 5 is an enlarged view of the insertion tip portion of the trocar of FIG. 4;

FIG. 6 is a cross-sectional detail of the insertion tip portion of a trocar engaged in a coupling portion of an integrated connector;

FIG. 7 is a cross-sectional detail view of an alternative coupling arrangement for a trocar and connector;

FIG. 13 is a partial cross-sectional view of the multi-lumen catheter of FIG. 12 showing details of a construction for the distal end of the catheter;

FIG. 14 is a perspective view of the connector portion of the catheter shown in FIGS. 12 and 13.

DETAILED DESCRIPTION

For the purposes of the following description and the claims appended hereto, the relative term "proximal" refers to those portions of a catheter and components of the catheter which are nearest the insertion end of the catheter as it is inserted into an area of a patient's body being catheterized such as a blood vessel. Conversely, the relative term "distal" refers to those portions of a catheter and components of the catheter which are farthest from the insertion end of the catheter.

Figure 1:
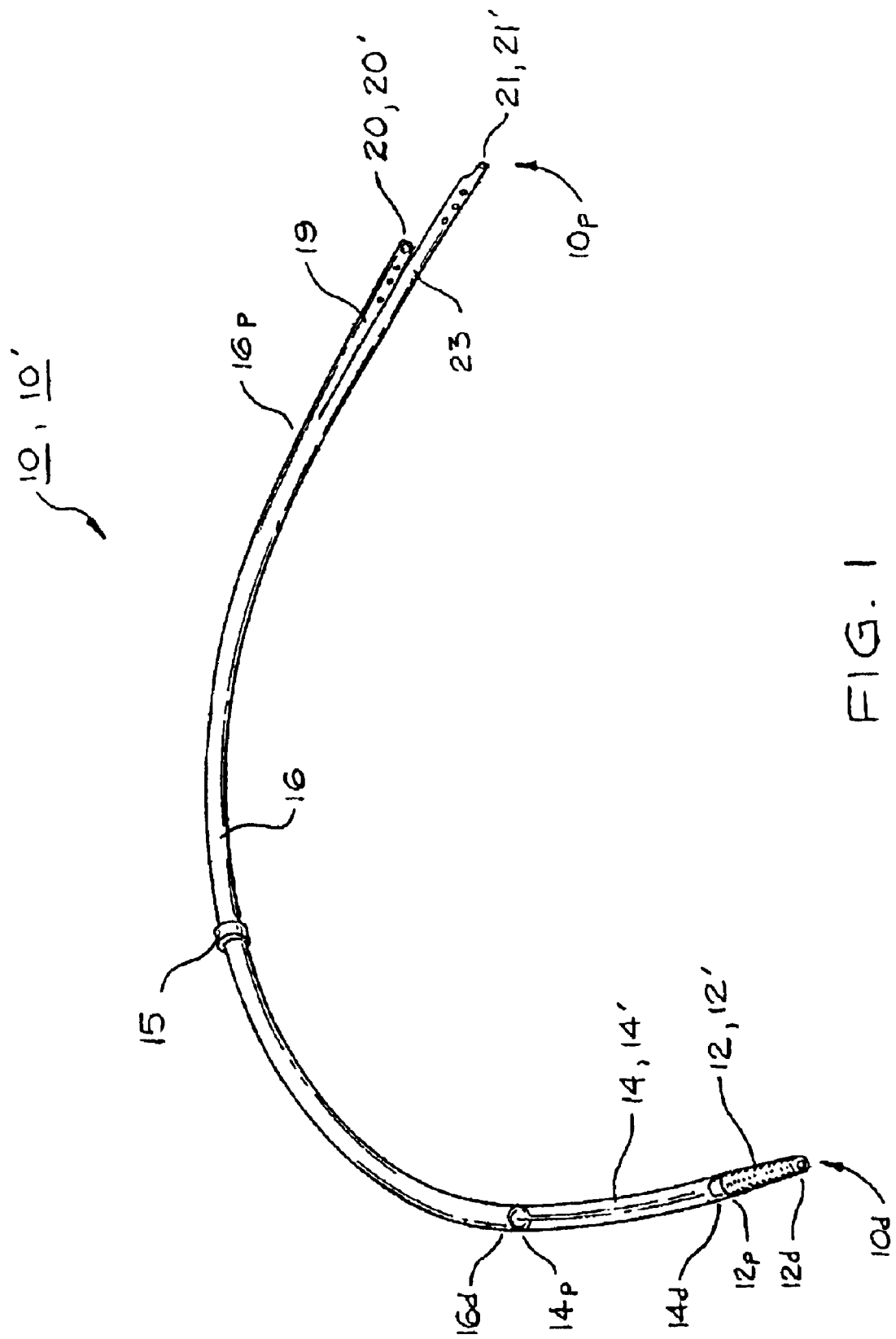
FIG. 1 is a perspective view of a multi-lumen catheter with an integrated connector.

An embodiment of a multi-lumen catheter 10 is shown in FIG. 1. The catheter 10 includes a multi-lumen catheter tube 16, a flush tube portion 14, and a connector 12. The catheter 10 includes a proximal end 10p and a distal end 10d. Similarly, each of the catheter components also include proximal and distal portions as follows: catheter tube 16 includes a proximal end 16p and a distal end 16d; flush tube portion 14 includes a proximal end 14p and a distal end 14d; and connector 12 includes a proximal end 12p and a distal end 12d as shown in FIG. 1.

Figure 2:
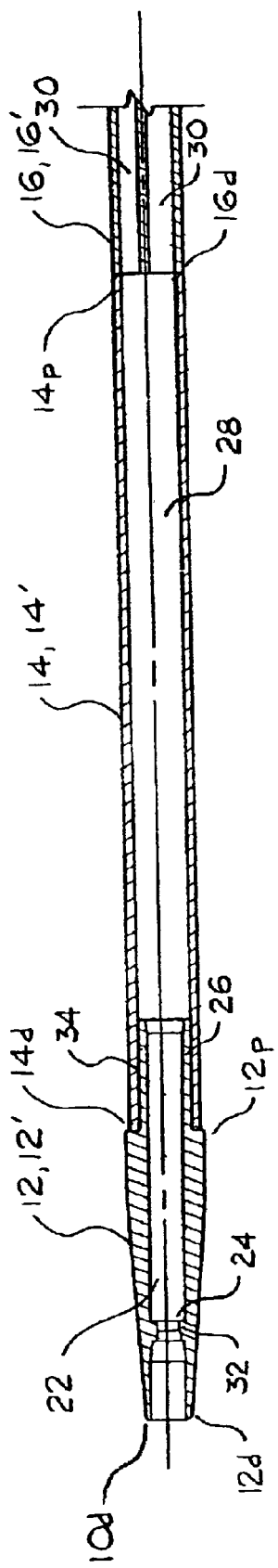
FIG. 2 is a cross-sectional view of a distal portion of the catheter of FIG. 1 taken through a longitudinal axis of the catheter shown in FIG. 1.

FIG. 2 shows a longitudinal cross-section of catheter 10. As shown in FIG. 2, catheter tube 16 includes a plurality of lumens through its length. Preferably, catheter tube 16 is resiliently flexible and preferably has a substantially cylindrical outer shape. The proximal end 14p of flush tube portion 14 is connected to the distal end 16d of catheter tube 16 as shown. The single lumen 28 of flush tube portion 14 is in fluid communication with each of the lumens 30 of the catheter tube 16. Flush tube portion 14 is also preferably flexibly resilient and preferably has a substantially cylindrical shape. Catheter tube 16 and flush tube portion 14 preferably have substantially equal outer diameters. Preferably, the proximal end 14p of flush tube portion 14 is heat welded to the distal end 16d of catheter tube 16 such that the junction has a substantially smooth and continuous outer contour.

As shown in FIG. 1, the proximal end of the catheter 10 may include a plurality of single-lumen extension tubes 19, 23. Each extension tube 19, 23 is connected to the proximal end 16p of the multi-lumen catheter tube 16 such that the single lumen of each extension tube 19, 23 is in fluid communication with one of the lumens 30 of the catheter tube 16. The extension tubes 19, 23 have outer walls, which may include one or more openings 20, 21 therein to provide for fluid flow into or from the extension tubes 19,23.

The proximal end 12p of the connector 12 is connected to the distal end 14d of the flush tube portion 14. A longitudinal cavity or bore 22 extends through the length of the connector 12 as shown in FIG. 2. The cavity 22 is in fluid communication with the single lumen 28 of the flush tube portion 14. Preferably, the proximal end 12p of the connector 12 includes a longitudinal spigot 26 as shown in FIG. 2. Preferably, spigot 26 has an outer diameter which is substantially equal to an inner diameter of the lumen 28 at the distal end 14d of the flush tube portion 14. The spigot 26 is matingly engaged in the lumen 28 as shown in FIG. 2. An adhesive 34 may affix the spigot 26 in the distal end 14d of the flush tube portion 14. Preferably, the proximal end 12p of the connector 12 has an outer diameter that is substantially equal to the outer diameter of the distal end 14d of the flush tube portion 14. The outer profile of the connector 12 may be tapered as indicated in FIG. 2, wherein the outer diameter at the proximal end 12p of the connector 12 is larger than the outer diameter of the connector 12 at its distal end 12d.

Figure 3:
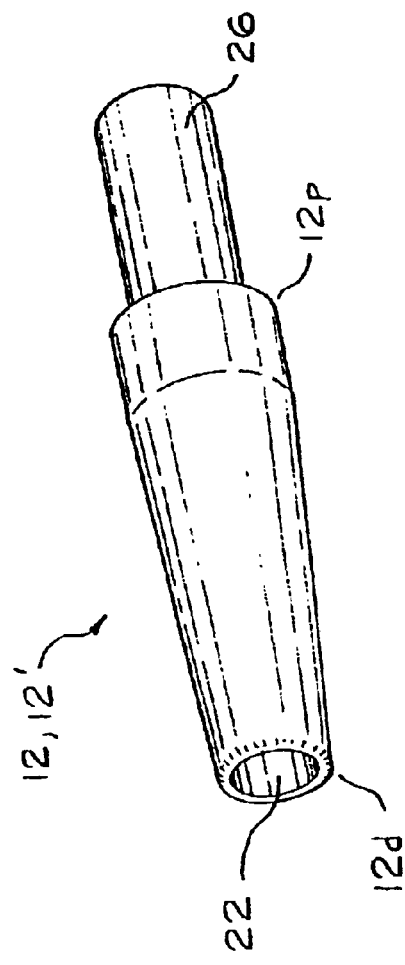
FIG. 3 is an enlarged perspective view of an integrated connector for the catheter of FIG. 1.

Connector 12 includes a coupling portion 24 near its distal end 12d. The coupling portion 24 is configured for secure mating engagement with a corresponding coupling portion of a medical device such as a trocar, a syringe, or the like. Coupling portion 24 of the connector may include a circumferential collar 32 as shown in FIGS. 2 and 3.

FIG. 4 shows a trocar 40 which may be used with the multi-lumen catheter 10 described above. The trocar 40 includes a shaft 41 having an insertion end or tip 42 and a handle end 44. A handle 46 is preferably provided which is configured to be securely gripped in a persons hand. As shown in FIG. 4, the trocar 40 may be constructed from a single piece of ductile or malleable material such as stainless steel or the like. The portion of the shaft 41 near the insertion tip 42 of the trocar 40 is preferably tapered as shown, and culminates in a pointed or slightly rounded tip 42. The trocar 40 may have any configuration which is can be used to form a subcutaneous tunnel in a patient suitable for receiving the catheter 10. As shown in FIG. 5, the trocar 40 includes a coupling portion 48 near the insertion tip 42. Preferably, the coupling portion 48 includes a circumferential groove 49. The groove 49 is sized and shaped to be engaged with the collar 32 of the connector 12 as shown in FIG. 6. The collar 32 snaps into the groove 49 as the insertion tip 42 of the trocar 40 is inserted into the open end of the cavity 22 at the distal end 12d of the connector 12, thereby lockably engaging the coupling portions 48, 24 of the trocar 40 and connector 12. Alternatively, as shown in FIG. 5, spiral grooves 47 or threads may be provided on the insertion tip 42 adjacent to the groove 49. By rotating the shaft 41 of the trocar 40 relative to the connector 12, the spiral grooves 47 act to advance the insertion tip 42 into the connector 12 until the groove 49 is in position to engage the collar 32.

In an alternative arrangement as shown in FIG. 7, the coupling portion 24 of the connector 12 may include a plurality of female threads 52. Alternatively, the connector 12 may not be threaded, and the male threads of the trocar 40 could be self tapping. Correspondingly, the coupling portion 48 of the trocar 40 may include a plurality of mating male threads 50. The male threads 50 are threaded into the female threads 52 to lockably engage the trocar 40 in the connector 12. Once lockably engaged in the connector 12, the trocar 40 can be used to guide the catheter 10 through the tunnel 106.

Figure 8:
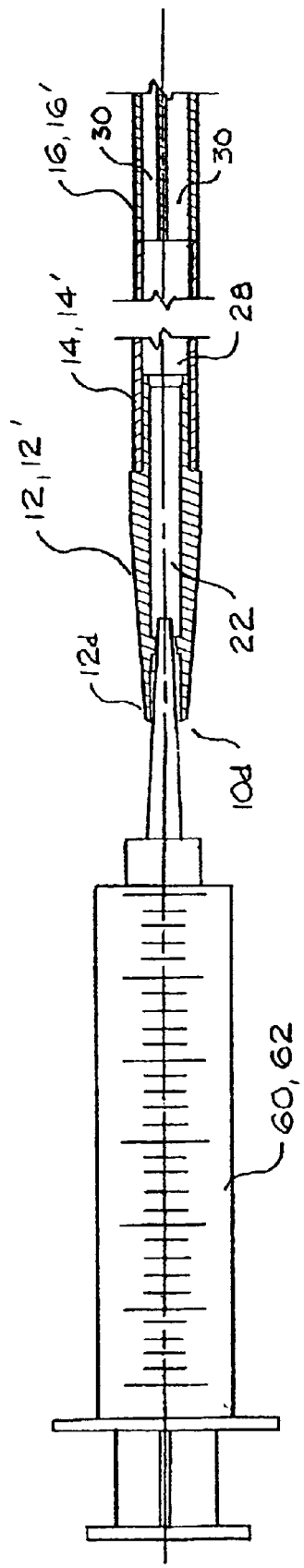
FIG. 8 is a cross-sectional view showing a flushing arrangement for the catheter of FIG. 1.

The connector 12 and flush tube portion 14 permit the simultaneous flushing of the multiple lumens 30 of the catheter tube 16 with a flushing liquid 62. As shown in FIG. 8, a tip of a syringe 60 or other flushing device may be inserted into the coupling portion 24 at the distal end 12d of the connector 12. Flushing liquid 62, such as a saline solution, can be injected through the cavity 22 of the connector 12, through the single lumen 28 of the flush tube portion 14, and into each of the lumens 30 of catheter tube 16. In this way, each of the plurality of catheter lumens 30 need not be separately flushed in a sequential manner, thereby saving both time and effort during the catheterization process.

Figure 12:
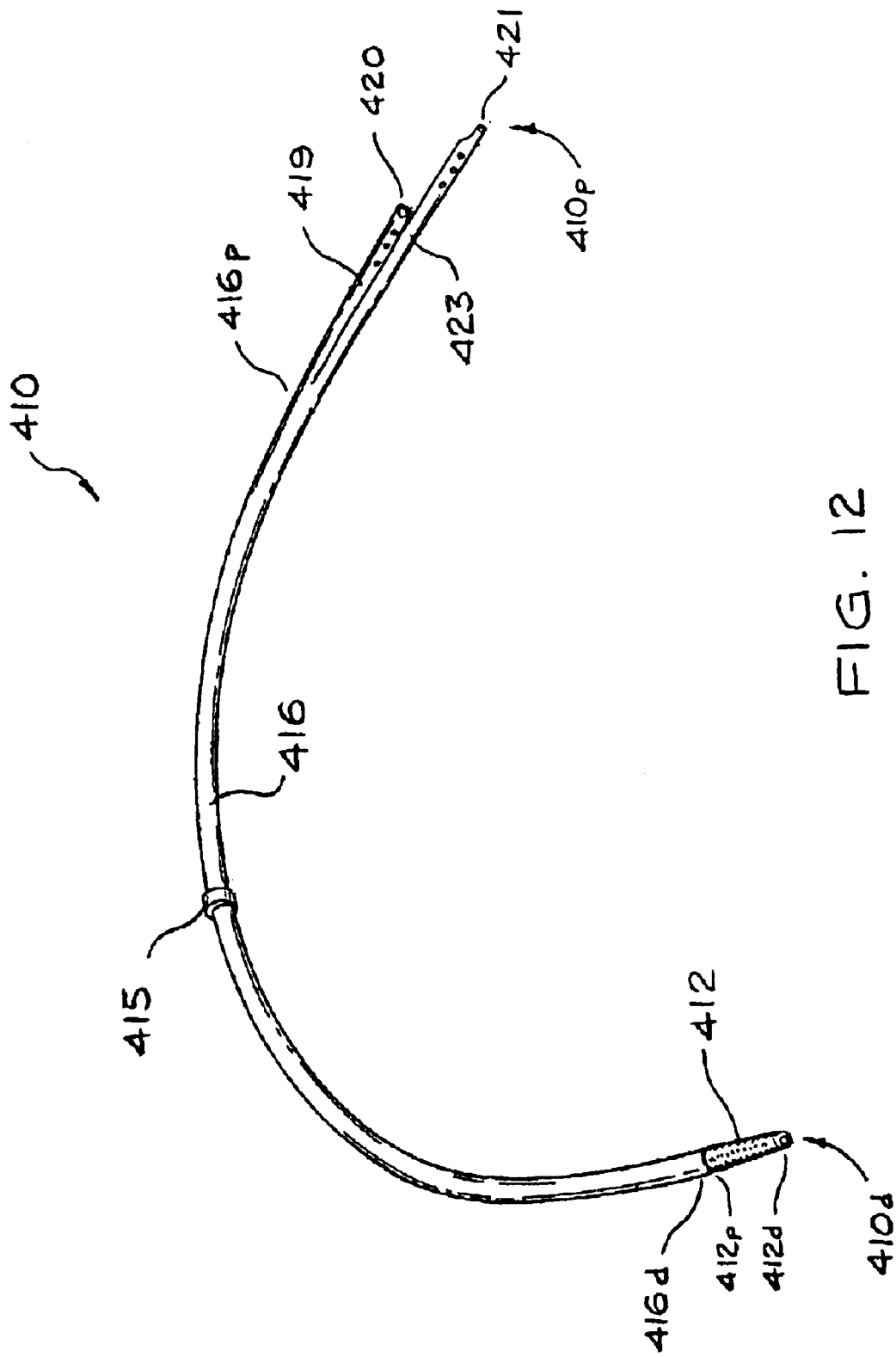
FIG. 12 is a perspective view of another embodiment of a multi-lumen catheter with an integrated connector.

An alternative embodiment 410 of a multi-lumen catheter is shown in FIGS. 12–15. This embodiment 410 is similar to the embodiment 10 described above, but does not include a flush tube portion. As shown in FIG. 12, the connector 412 is connected directly to the distal end 416d of the multi-lumen catheter tube 416. The proximal end 410p of the multi-lumen catheter 410 may include a plurality of single-lumen extension tubes 419, 423. Each extension tube 419, 423 is connected to the proximal end 416p of the multi-lumen catheter tube 416 such that the single lumen of each extension tube 419, 423 is in fluid communication with one of the lumens of the multi-lumen catheter tube 416. The extension tubes 419, 423 have outer walls, which may include one or more openings 420, 421 therein to provide for fluid flow into or from the extension tubes 419, 423. A stabilizing cuff 415 may be provided on the catheter 410 as shown in FIG. 12.

Figure 15:
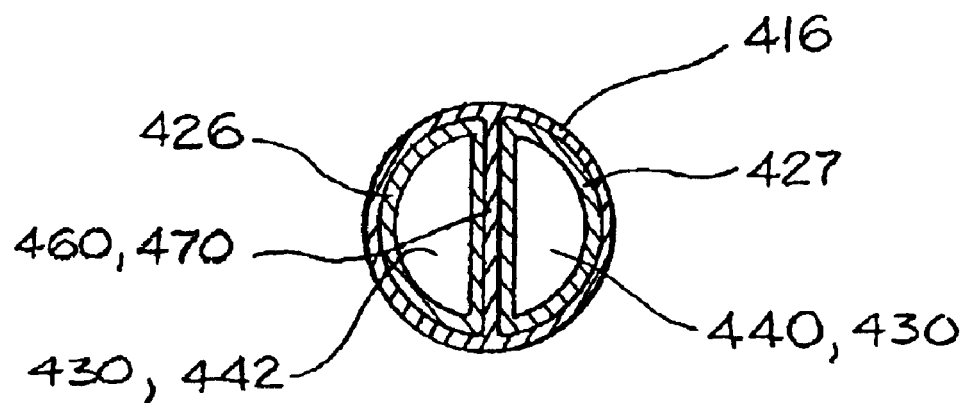
FIG. 15 is a cross-sectional view taken through line I—I as shown in FIG. 13.

As shown in FIGS. 13–15, the connector 412 is adapted to engage the multiple lumens 430 of the catheter tube 416. The connector 412 may include a plurality of prongs 426, 427 extending longitudinally from its proximal end 412p. One or more slots 470 may divide the prongs 426, 427. To affix the connector 412 to the distal end 416d of the catheter tube 416, the prongs 426, 427 are engaged in the lumens 430 as shown in FIG. 13. The prongs 426, 427 may be permanently joined to the catheter tube 416 with a suitable adhesive. Alternatively, the prongs 426, 427 may be sized slightly larger than the lumens 430 and/or may include non-smooth outer surfaces (such as circumferential ridges, barbs, grooves, or the like) to form a frictional fit between the inner walls of the lumens 430 and the prongs 426, 427 (not shown).

In order to permit simultaneous flushing of the multiple lumens 430, longitudinal passages 440, 442 may be provided through each of the prongs as shown in FIG. 13. Each of the passages 440, 442 is in fluid communication with a longitudinal cavity 422 in the distal end 412d of the connector 412. In this arrangement, a plurality of substantially parallel flow-paths are defined through the connector 412 from its distal end 412d to the adjoining lumens 430 in the catheter tube 416. The distal end 412d of the connector 412 may be substantially the same as the embodiment 12 of the connector as described above and shown in FIGS. 2, 3, and 6–8. For example, as shown in FIG. 13, the connector 412 may include a circumferential collar 432 in its cavity 422 for mating engagement with a trocar 40 as described above.

Figure 9A:
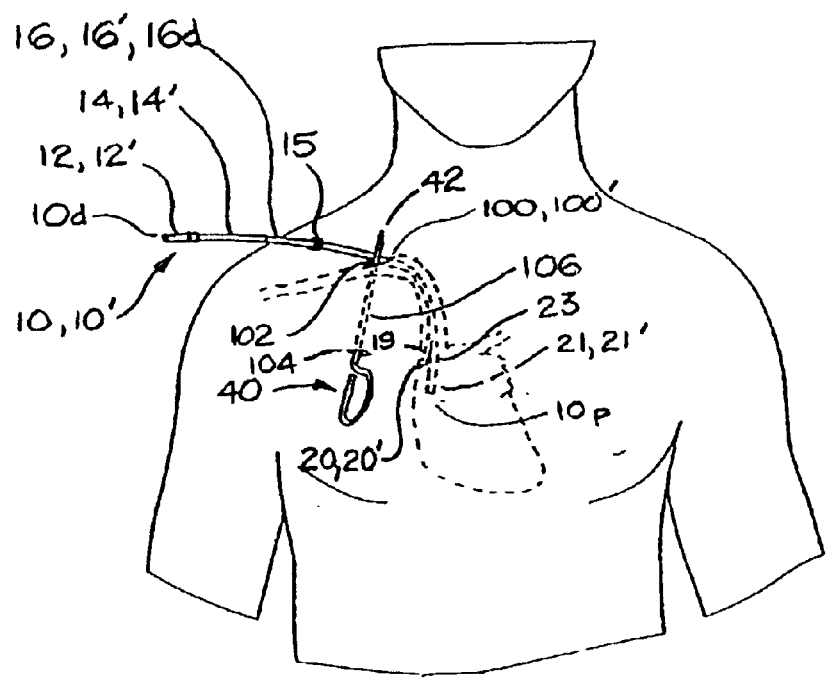
FIGS. 9A–9D illustrate a method of inserting a multi-lumen catheter with an integrated connector as shown in FIG. 1 into a patient.

When the multi-lumen catheter tube 416 includes two lumens 430, the lumens 430, prongs 426, 427, and passages 440, 442 may have corresponding substantially D-shaped cross sections as shown in FIG. 15. In this arrangement, the D-shaped lumens 430 are separated by a divider wall or septum 460 which is received in a slot 470 between the D-shaped prongs 426, 427. A catheter 10, 410 like that described above can be used in an improved method of inserting a multiple-lumen catheter into a patient. One embodiment of such a method is sequentially illustrated in FIGS. 9A–9D. While the method is described in terms of inserting embodiment 10 of the catheter as described in detail above, the improved method can also be used for inserting alternate embodiment 410 of the multi-lumen catheter or any other similarly constructed catheter having an integrated connector on its distal end. As shown in FIG. 9A, the proximal tips 20, 21 of the catheter 10 are accurately placed in a patient's blood vessel through an incision 100 in the patient's skin. After tip placement, distal portions of the catheter 10 protrude from the patient's skin at the incision 100, including the distal tip 10d, the connector 12, the flush tube portion 14, and the distal end 16d of the catheter tube 16. As also shown in FIG. 9A, a subcutaneous tunnel 106 is formed using the trocar 40. The tunnel 106 includes a first end 102 and a second end 104. The first end 102 is preferably coincident with the incision 100. At this point, the multiple lumens 30 of the catheter tube 16 may be simultaneously flushed with a flushing liquid 62 using a syringe 60 or the like as shown in FIG. 8. Note that the trocar 40 is positioned in the tunnel 106 such that the insertion tip of the trocar protrudes from the first end 102 of the tunnel 106 as shown in FIG. 9A.

Figure 9B:
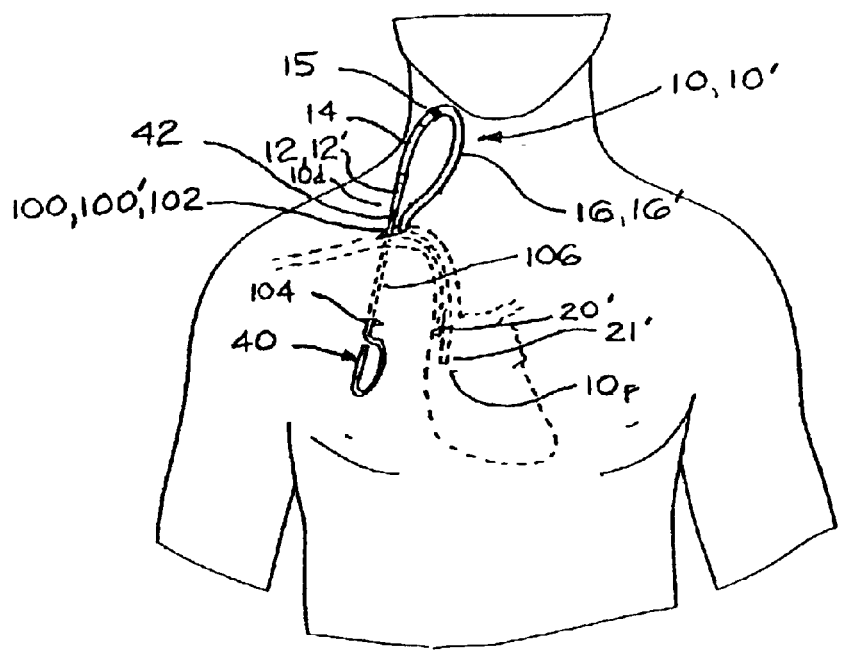
Figure 9C:
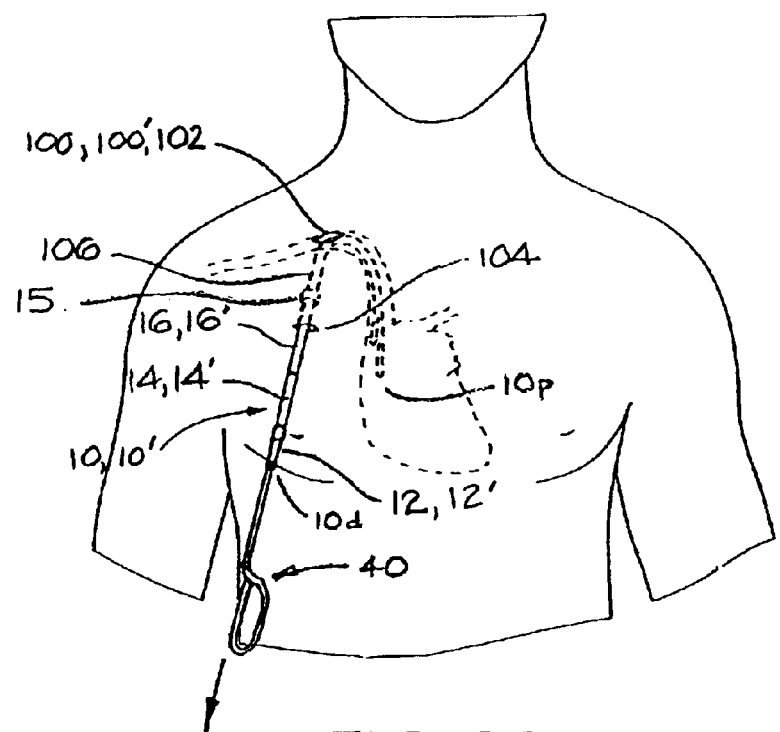

Referring to FIG. 9B, the insertion tip 42 of the trocar 40 is inserted into the distal tip 10b of the catheter 10 and into the cavity 22 of the connector 12 to lockably engage the coupling portion 48 of the trocar 40 with the mating coupling portion 24 of the connector 12 as shown in detail in FIG. 6. Once the connector 12 and trocar 40 are connected, the connector 12, flush tube portion 14, and the distal end 16d of the catheter tube 16 are guided and drawn through the tunnel 106 with the trocar 40 as shown in FIG. 9C. Preferably, the distal end 16d of the catheter tube 16 is drawn sufficiently through the tunnel 106 such that no portion of the catheter tube 16 protrudes from the patient at the incision 100 at the insertion point.

Figure 9D:
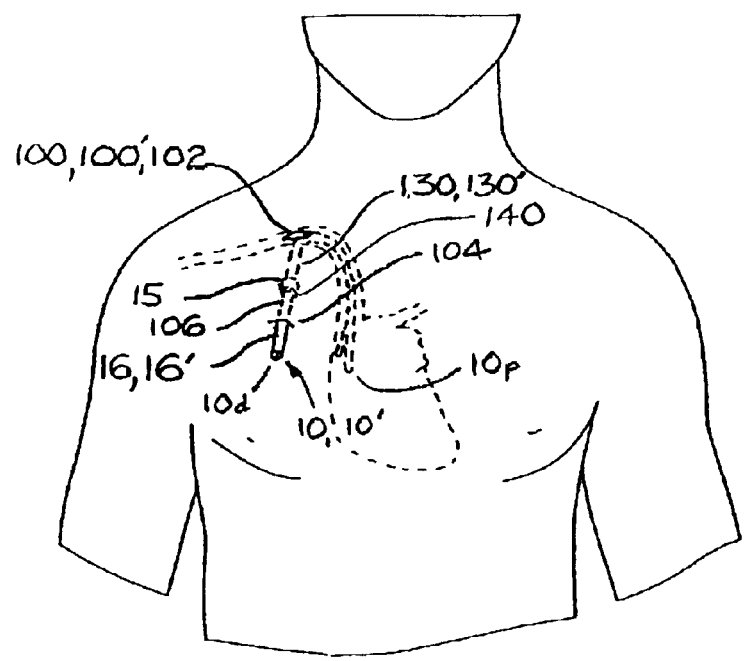
Figure 10:
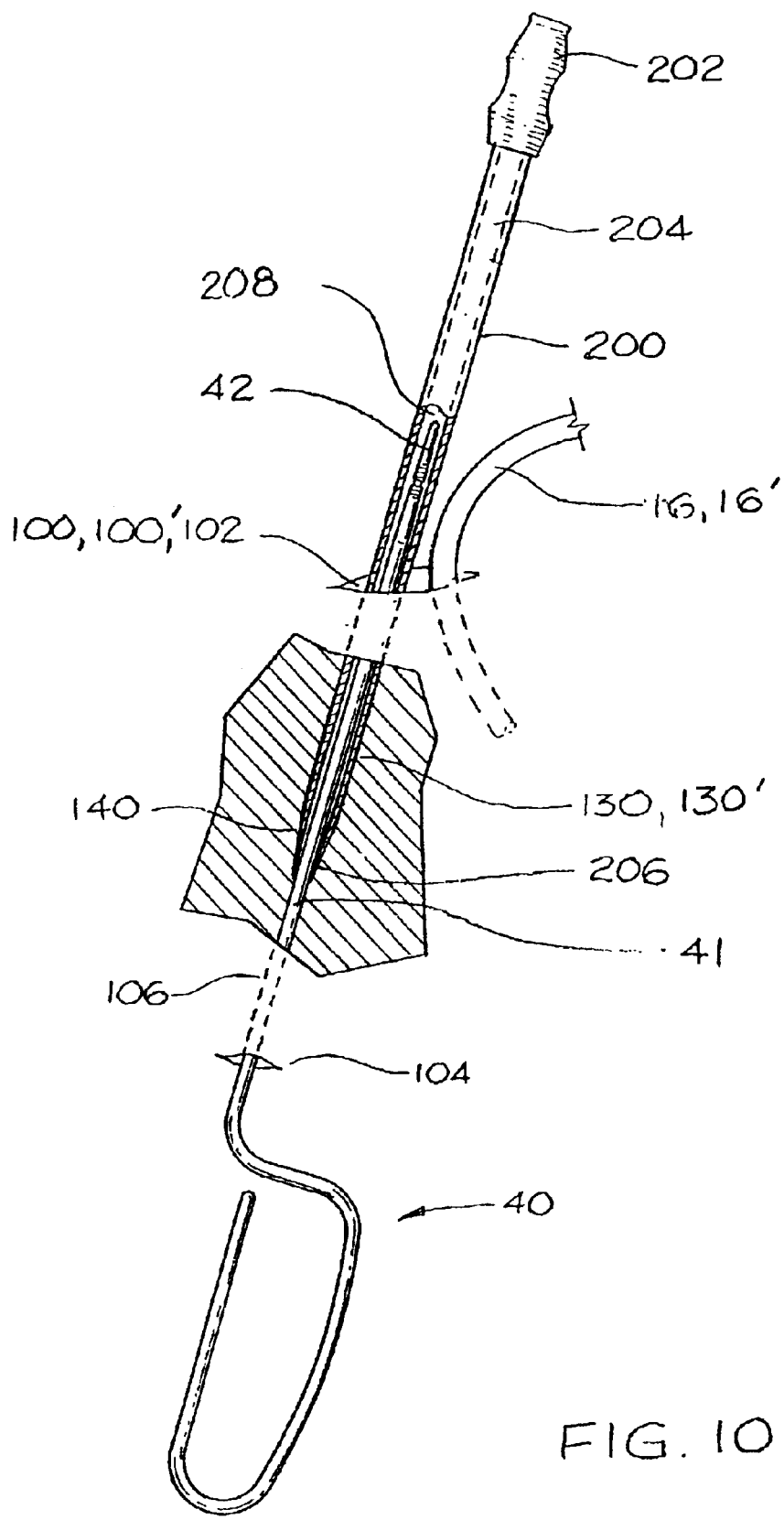
FIG. 10 is a partial sectional view of a sheath dilator that slides along a trocar to dilate a portion of a subcutaneous tunnel in a patient.

An outer portion of the catheter tube 16 may include a tissue in-growth stabilizing cuff 15 for stabilizing the inserted catheter 10 in the patient. Referring to FIG. 9D, when the catheter 10 includes a stabilizing cuff 15, a portion 130 of tunnel 106 may be dilated to enlarge the width of the tunnel 106 to better receive the cuff 15 as the catheter 10 is drawn through the tunnel 106. As shown in FIG. 10, the dilated portion 130 of the tunnel is preferably dilated by sliding a sheath dilator 200 over the insertion tip 42 and along shaft 41 of the trocar 40 when the trocar 40 is positioned in the subcutaneous tunnel 106. The sheath dilator 200 preferably includes a hollow bore 208, a tapered leading end 206, a substantially cylindrical portion 204, and a handle 202. The sheath dilator 200 is inserted through the first end 102 of the tunnel 106 and into the tunnel 106 until the tip 206 has been inserted proximate to a cuff seating point 104 in the tunnel 106 to form a dilated portion 130 of the tunnel 106. Once the dilated portion 130 is sufficiently dilated, the sheath dilator 200 is removed from the tunnel 106 and the trocar 40. The insertion tip 42 of the trocar 40 is then engaged with the connector 12 as shown in FIG. 9B, and the distal end 10b of the catheter 10 is drawn sufficiently through the tunnel 106 such that the cuff 15 seats at an end 140 of the dilated portion 130 of the tunnel 106 as shown in FIG. 9D.

Figure 11:
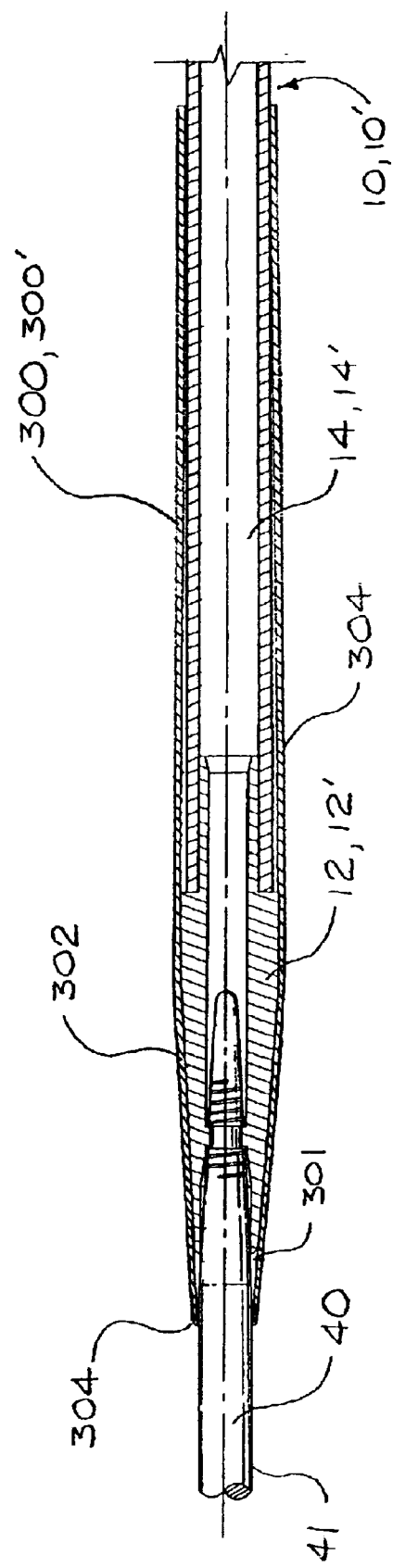
FIG. 11 is cross-sectional view of a sheath assembled about an interconnected trocar, connector, and flush tube portion.

As shown in FIG. 11, a sheath 300 may be placed over outer portions of the interconnected trocar 40, connector 12, and flush tube portion 14 to facilitate passage of distal portions of the catheter 10 through a subcutaneous tunnel 106. The sheath 300 preferably includes a hollow bore 301, a tapered outer portion 302, and a cylindrical outer portion 304. In order to assemble the sheath 300 as shown, the sheath 300 is back-fitted over the shaft 41 of the trocar 40 before the trocar 40 is engaged with the connector 12 (not shown). After the trocar 40 and the connector 12 are connected, the sheath 300 is positioned over at least a portion of the trocar 40, the connector 12, and at least a portion of the flush tube portion 14 as shown in FIG. 11. The sheath 300 includes an outer contour which is sufficiently smooth in both shape and surface texture to pass through a subcutaneous tunnel 106 together with the catheter 10 without substantial frictional resistance. The sheath 300 masks any discontinuities at the interfaces between outer surfaces of the trocar 40 and the connector 12 and between outer surfaces of the connector 12 and the flush tube portion 14, thereby providing the trocar/catheter assembly with an outer contour that is more easily passed through a subcutaneous tunnel. Preferably, the sheath 300 includes a leading tip portion 304 which has an outer diameter substantially equal to the diameter of the trocar 40 as shown, such that there is little or no discontinuity formed between outer portions of the shaft 41 of the trocar 40 and the adjacent leading tip portion 304 of the sheath 300.

Once the catheter 10 is tunneled as described above and the connector 12, flush tube portion 14, and a distal portion of the catheter tube 16 are severed from the remainder of the catheter tube 16, the catheter 10 is ready for connection to a fluid management device such as a dialysis machine. Preferably, the tip of the multi-lumen catheter tube 16 protruding from the incision 104 (as shown in FIG. 9D) is attached to a selectively attachable hub as described in co-pending applications Ser. Nos. 09/769,052 and 10/086,033, which have been incorporated by reference above. As shown in FIG. 3 of these applications, the cannulae 22a, 24a of the selectively attachable hub 20 are inserted into the lumens at the distal end of the multi-lumen catheter tube. As shown in FIG. 1 of these applications, the hub 20 is then releasably connected to the catheter tube by a compression sleeve 36 and compression cover 34. The extension tubes 26, 28 are then connected to a fluid management device with connectors 30, 32. The incisions 100 and 104 are dressed in an appropriate manner.

Preferably, the compression cover 34 and the compression sleeve 36 are "preloaded" onto the trocar 40 by placing the compression sleeve 36 and the compression cover 34 axially over the tip 42 of the trocar 40. A protrusion, such as a small piece of tape, can be wrapped around the trocar 40 between the tip 42 and the preloaded to prevent compression sleeve 36 and the compression cover 34 from inadvertently sliding off the trocar 40 before the trocar 40 and the connector 12 are connected. Before the connector 12, flush tube portion 14, and a distal portion of the catheter tube 16 are severed from the remainder of the catheter tube 16, the compression cover 34 and the compression sleeve 36 are moved from the trocar 40 onto the distal portion 16d of the catheter tube 16. The compression cover 34 and the compression sleeve 36 are then in a position to be fitted axially about the cannulae 22 and 24 so as to create force to prevent inadvertent separation of the catheter tube 12 from the hub 20.

The invention also includes a method of replacing a multi-lumen catheter 10 which has been tunneled in a patient as described above. First, the selectively attachable hub is removed from the distal end of the catheter tube 16. Next, the catheter tube 16 is withdrawn from the subcutaneous tunnel 106 from the first end 102 of the tunnel 106. The proximal portions of the catheter 10 are then withdrawn from the patient through an incision 100'. A replacement multi-lumen catheter 10' with an integrated connector 12' is then tunneled in a patient by a procedure similar to that described above, but using the same subcutaneous tunnel 106 formed in the patient for the original catheter 10 as shown in FIGS. 9A–9D. Once the catheter tips 20', 21' of the replacement catheter 10' are accurately positioned in the patient through incision 100', a trocar 40 is inserted through the pre-formed tunnel 106 such that the insertion tip 42 of the trocar 40 outwardly extends from the first end 102 of the tunnel 106 as shown in FIG. 9A. A portion of the tunnel 130' may be re-dilated as necessary as described above and as shown in FIGS. 9D and 10. A sheath 300' may then be back-fitted over the insertion tip 42 and the shaft 41 of the trocar 40. The connector 12' of the replacement catheter 10' is connected to the tip 42 of the trocar 40 as shown in FIG. 9B. The sheath 300' may then be positioned over portions of the catheter 10' as shown in FIG. 11. The replacement catheter 10' is then guided through the tunnel 106 with the trocar 40 until the replacement catheter 10' is finally positioned in the patient as shown in FIG. 9C. After severing the trocar 40, connector 12', flush tube portion 14', and a distal portion of the catheter tube 16' from the remainder of the catheter tube 16' as shown in FIG. 9D, the replacement catheter 10' is connected to a fluid management device as described above.

While this invention has been illustrated and described in accordance with a preferred embodiment, it is recognized that variations and changes may be made therein without departing from the invention as set forth in the claims. Certain modifications and improvements will occur to those skilled in the art upon a reading of the forgoing description. For example, the connection means between the integrated connector and the trocar may be configured in any suitable manner which provides a secure connection. Also by way of example, the process steps of forming a subcutaneous tunnel and extending a trocar through the tunnel may occur simultaneously rather than as discrete steps. It should be understood that all such modifications are not contained herein for the sake of conciseness and readability, but are properly within the scope of the following claims.

What is claimed is:

1. A method of inserting a multi-lumen catheter in a patient, wherein the multi-lumen catheter includes a multi-lumen catheter tube having a proximal end with proximal tips and a distal end, a single-lumen flush tube portion having a proximal end connected to the distal end of the catheter tube and a distal end, and an integrated connector including a coupling portion on a distal end of the connector and having a proximal end connected to the distal end of the flush tube portion, the method comprising:

(a) inserting the proximal end of the multi-lumen catheter tube through an incision in the patient's skin and placing the proximal tips of the catheter in the patient, such that distal portions of the multi-lumen catheter tube, the flush tube portion, and the connector extend outwardly from the patient through the incision;

(b) forming a subcutaneous tunnel having a first end proximate to the incision, and an opposed second end which is remote from the first end;

(c) inserting a trocar through the tunnel from the second end to the first end of the tunnel such that a protruding tip of the trocar protrudes from the patient through the first end of the tunnel, the trocar including a coupling portion adjacent said protruding tip of the trocar;

(d) engaging the coupling portion of the trocar in the coupling portion of the connector;

(e) guiding the connector, the flush tube portion, and at least a portion of the distal end of the catheter tube through the tunnel and out through the second end of the tunnel with the trocar until the catheter tube is finally positioned in the tunnel; and (f) severing the connector and engaged trocar, the flush tube portion, and a portion of the multi-lumen catheter tube near its distal end from a remaining portion of the multi-lumen catheter tube.

2. A method according to claim 1 wherein the multi-lumen catheter includes an in-growth stabilizing cuff affixed to a portion of an outer surface of a distal portion of the catheter tube protruding from the first incision, the method further comprising dilating a portion of the tunnel between the first end of the tunnel and a cuff seating point in the tunnel before engaging the coupling portion of the trocar in the coupling portion of the connector, and wherein the catheter tube is finally positioned in the tunnel when the stabilizing cuff is seated at the cuff seating point in the tunnel.

3. A method according to claim 2, wherein dilating a portion of the tunnel includes sliding a sheath dilator having a substantially hollow bore and a dilating outer surface along the trocar and into the first end of the tunnel.

4. A method according to claim 1, the method further comprising flushing the catheter lumens by injecting a flushing liquid through the distal end of the connector, the connector cavity, and the flush tube portion before engaging the coupling portion of the trocar in the coupling portion of the connector.

5. A method according to claim 1 further comprising placing a sheath having a smooth outer surface and a substantially hollow bore over at least a portion of the trocar, the connector, and at least a portion of the flush tube portion before guiding the connector through the tunnel with the trocar.

6. A method according to claim 5 wherein placement of the sheath includes back-fitting the sheath over the trocar before engaging the coupling portion of the trocar in the coupling portion of the connector, and sliding the sheath over at least a portion of the trocar, the connector, and at least a portion of the flush tube portion.

7. A method according to claim 1 further comprising:
(a) providing a selectively attachable hub assembly including a hub body with a distal portion and a proximal portion;
(b) selectively attaching the proximal portion of the hub body to a distal portion of the remaining portion of the multi-lumen catheter tube; and
(c) connecting the proximal portion of the hub assembly to a fluid management device.

8. A method according to claim 1 further comprising:
(a) withdrawing distal portions of the catheter tube from the subcutaneous tunnel through the first end of the tunnel;
(b) withdrawing the proximal end of the multi-lumen catheter tube from the patient;
(c) providing a replacement multi-lumen catheter including a multi-lumen catheter tube having a proximal end with proximal tips and a distal end, a single-lumen flush tube portion having a proximal end connected to the distal end of the catheter tube and a distal end, and an integrated connector including a coupling portion on a distal end of the connector and having a proximal end connected to the distal end of the flush tube portion;
(d) inserting the proximal end of the catheter tube of the replacement multi-lumen catheter through a replacement incision in the patient's skin proximate to the first end of the tunnel, and placing the proximal tips of the replacement multi-lumen catheter in the patient, such that a distal portion of the multi-lumen catheter tube, the flush tube portion, and the connector of the replacement multi-lumen catheter extend outwardly from the patient through the replacement incision;
(b) inserting a trocar through the subcutaneous tunnel from the second end to the first end of the tunnel such that a protruding tip of the trocar protrudes from the patient through the first end of the tunnel, the trocar including a coupling portion adjacent said protruding tip of the trocar;
(d) engaging the coupling portion of the trocar in the coupling portion of the connector of the replacement multi-lumen catheter;
(e) guiding the connector, the flush tube portion, and at least a portion of the distal end of the catheter tube of the replacement multi-lumen catheter through the tunnel and out through the second end of the tunnel with the trocar until the replacement catheter tube is finally positioned in the tunnel; and
(f) severing the connector and engaged trocar, the flush tube portion, and a distal portion of the multi-lumen catheter tube of the replacement multi-lumen catheter from a remaining portion of the multi-lumen catheter tube of the replacement catheter.

9. A method of inserting a multi-lumen catheter in a patient, wherein the multi-lumen catheter includes a multi-lumen catheter tube having a proximal end with proximal tips and a distal end, and an integrated connector including a coupling portion proximate to a distal end of the connector and having a proximal end connected to the distal end of the multi-lumen catheter tube, the method comprising:
(a) inserting the proximal end of the multi-lumen catheter tube through an incision in the patient's skin and placing the proximal tips of the catheter in the patient, such that distal portions of the multi-lumen catheter tube and the connector extend outwardly from the patient through the incision;
(b) forming a subcutaneous tunnel having a first end proximate to the incision, and an opposed second end which is remote from the first end;
(c) inserting a trocar through the tunnel from the second end to the first end such that a protruding tip of the trocar protrudes from the patient through the first end of the tunnel, the trocar including a coupling portion adjacent said protruding tip of the trocar;
(d) engaging the coupling portion of the trocar in the coupling portion of the connector;
(e) guiding the connector and at least a portion of the distal end of the catheter tube through the tunnel and out through the second end of the tunnel with the trocar until the catheter tube is finally positioned in the tunnel; and
(f) severing the connector and engaged trocar and a portion of the multi-lumen catheter tube near its distal end from a remaining portion of the multi-lumen catheter tube.

10. A method of inserting a multi-lumen catheter into a patient, wherein the multi-lumen catheter includes a first lumen and a second lumen, a proximal end and a distal end, the distal end including a single-lumen flush tube portion in fluid communication with said first lumen and said second lumen and a coupling portion, the method comprising:
(a) inserting the proximal end of the multi-lumen catheter into the patient through an incision in the patient's skin, such that a portion of the multi-lumen catheter including the distal end thereof extends outwardly from the patient through the incision;
(b) forming a subcutaneous tunnel having a first end adjacent said incision and a second end which is remote from the first end;
(i) inserting a trocar through the tunnel from the second end to the first end such that a protruding tip of the trocar protrudes from the patient through the first end of the tunnel, the trocar including a coupling portion adjacent said protruding tip of the trocar;
(c) engaging the coupling portion of the trocar with the coupling portion of the catheter;
(d) guiding the trocar and the attached catheter through the tunnel so that the catheter is positioned in the tunnel; and
(e) severing the single-lumen flush tube portion and the coupling portion from a remaining portion of the multi-lumen catheter.

11. A method according to claim 10 wherein the multi-lumen catheter includes an in-growth stabilizing cuff affixed to a portion of an outer surface of the catheter.

12. A method according to claim 11 further comprising placing the stabilizing cuff between the outer surface of the catheter and an inner surface of the subcutaneous tunnel.

13. A method according to claim 11 further comprising dilating a portion of the tunnel between the first end of the tunnel and a cuff seating point in the tunnel before engaging the trocar with the coupling portion of the catheter, and positioning the catheter in the tunnel such that the stabilizing cuff is seated proximate the cuff seating point in the tunnel.

14. A method according to claim 13, wherein dilating a portion of the tunnel includes sliding a sheath dilator having a substantially hollow bore and a dilating outer surface along the trocar and into the first end of the tunnel.

15. A method according to claim 10, further comprising simultaneously flushing the first and second catheter lumens by injecting a flushing liquid through the single-lumen flush tube portion of the distal end of the catheter before engaging the trocar with the coupling portion of the catheter.

16. A method according to claim 10 further comprising placing a sheath having a smooth outer surface and a substantially hollow bore over a portion of the trocar and the coupling portion of the catheter before guiding the trocar and the coupling portion of the catheter through the tunnel.

17. A method according to claim 16 wherein placement of the sheath includes back-fitting the sheath over the trocar before engaging the trocar with the coupling portion of the catheter, and sliding the sheath over the portion of the trocar and the coupling portion of the catheter after the trocar and coupling portion are engaged.

18. A method according to claim 10 further comprising:
(a) providing a selectively attachable hub including a hub body with a distal portion and a proximal portion;
(b) selectively attaching the proximal portion of the hub body to the catheter; and
(c) connecting the distal portion of the hub assembly to a fluid management device.

19. A method according to claim 10 wherein the single-lumen flush-tube portion and the coupling portion of the catheter are of a different material than the remainder of the catheter.

20. A method according to claim 10 wherein the coupling portion and the single-lumen flush tube portion are formed as a single element.

21. A method according to claim 20 wherein the single-lumen flush tube portion including the coupling portion is of a different material than the remainder of the catheter.

22. A method according to claim 10 wherein the single-lumen flush tube portion and the coupling portion are of a different material than the remainder of the catheter, the single-lumen flush tube portion and the coupling portion being firmly attached to the multi-lumen catheter adjacent a distal end of each of the first lumen and second lumen of the multi-lumen catheter.

23. A method of inserting a catheter into a patient, wherein the catheter includes a multi-lumen portion having a proximal end and a distal end, and a connector comprising a coupling portion and a single-lumen portion, the single-lumen portion is in fluid communication with the distal end of the multi-lumen portion of the catheter, the method comprising:
(a) inserting the proximal end of the catheter into the patient through an incision in the patient's skin, such that a portion of the catheter extends outwardly from the patient through the incision;
(b) forming a subcutaneous tunnel having a first end adjacent said incision and a second end which is remote from the first end;
    (i) inserting a trocar through the tunnel from the second end to the first end such that a protruding tip of the trocar protrudes from the patient through the first end of the tunnel, the trocar including a coupling portion adjacent said protruding tip of the trocar;
(c) engaging the coupling portion of the trocar with the coupling portion of the catheter;
(d) guiding the connector and at least a portion of the multi-lumen portion of the catheter through the tunnel with the trocar; and
(e) separating the connector and engaged trocar from the catheter, leaving a portion of the catheter extending outwardly from the patient through one of the ends of the subcutaneous tunnel.

24. A method according to claim 23 wherein the multi-lumen portion of the catheter includes an in-growth stabilizing cuff affixed to an outer surface of the multi-lumen portion.

25. A method according to claim 24 further comprising placing the stabilizing cuff between the outer surface of the multi-lumen portion and an inner surface of the subcutaneous tunnel.

26. A method according to claim 25 further comprising dilating a portion of the tunnel between the first end of the tunnel and a cuff seating point in the tunnel before engaging the coupling portion of the trocar with the coupling portion of the connector, and positioning the multi-lumen portion of the catheter in the tunnel such that the stabilizing cuff is seated proximate the cuff seating point in the tunnel.

27. A method according to claim 26, wherein dilating a portion of the tunnel includes sliding a sheath dilator having a substantially hollow bore and a dilating outer surface along the trocar and into the first end of the tunnel.

28. A method according to claim 23, further comprising simultaneously flushing the first and second catheter lumens by injecting a flushing liquid through the single-lumen flush tube portion of the distal end of the catheter before engaging the coupling portion of the trocar with the coupling portion of the distal end of the catheter.

29. A method according to claim 23 further comprising placing a sheath having a smooth outer surface and a substantially hollow bore over the coupling portion of the trocar and the coupling portion of the connector before guiding the coupling portion of the trocar and the coupling portion of the connector into the first end of the tunnel and out the second end of the tunnel.

30. A method according to claim 29 wherein placement of the sheath includes back-fitting the sheath over the trocar before engaging the coupling portion of the trocar with the coupling portion of the connector, and sliding the sheath over the coupling portion of the trocar and the coupling portion of the distal end of the catheter after the coupling portions are engaged.

31. A method according to claim 23 further comprising:
(a) providing a selectively attachable hub including a hub body with a distal portion and a proximal portion; (b) selectively attaching the proximal portion of the hub body to the catheter; and
(c) connecting the proximal portion of the hub assembly to a fluid management device.

32. A method according to claim 23 wherein the connector is of a different material than the remainder of the catheter.

33. A method according to claim 23 wherein the connector is of a different material than the remainder of the catheter, the connector being firmly attached adjacent the distal end of the multi-lumen portion of the catheter.

34. A method according to claim 23 wherein the connector is of a different material than the remainder of the catheter, the connector being firmly attached to a distal end of a single-lumen portion of the catheter and the distal end of the multi-lumen portion of the catheter being firmly attached to a proximal end of the single-lumen portion of the catheter.

* * * * *